(12) United States Patent
Imran

(10) Patent No.: US 8,337,488 B2
(45) Date of Patent: Dec. 25, 2012

(54) DIAPHRAGM DRUG PUMP

(75) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 440 days.

(21) Appl. No.: 12/564,859

(22) Filed: Sep. 22, 2009

(65) Prior Publication Data

US 2010/0076413 A1      Mar. 25, 2010

Related U.S. Application Data

(60) Provisional application No. 61/099,196, filed on Sep. 22, 2008.

(51) Int. Cl.
*A61K 9/22* (2006.01)

(52) U.S. Cl. ............... 604/891.1; 604/132; 604/133; 604/153

(58) Field of Classification Search ............... 604/890.1, 604/891.1, 132, 133, 140, 141, 143, 152, 604/153

See application file for complete search history.

(56) References Cited

U.S. PATENT DOCUMENTS

| | | | |
|---|---|---|---|
| 4,886,514 A | 12/1989 | Maget | |
| 5,061,242 A | 10/1991 | Sampson | |
| 5,382,236 A | 1/1995 | Otto et al. | |
| 5,514,103 A | 5/1996 | Srisathapat et al. | |
| 5,722,957 A | 3/1998 | Steinbach | |
| 5,820,589 A | 10/1998 | Torgerson et al. | |
| 6,416,495 B1 * | 7/2002 | Kriesel et al. | 604/132 |
| 6,520,936 B1 | 2/2003 | Mann | |

OTHER PUBLICATIONS

International Search Report and Written Opinion mailed Apr. 19, 2010 in International App. No. PCT/US2009/057913 10 pages.

* cited by examiner

*Primary Examiner* — Bhisma Mehta

(74) *Attorney, Agent, or Firm* — Mahamedi Paradice Kreisman LLP

(57) ABSTRACT

Embodiments of the invention provide apparatus, systems and methods for delivering drugs using an implantable diaphragm based drug pump which can deliver precisely controlled doses of drug to selected target tissue sites in the brain, digestive system, blood stream heart or other selected site. Various embodiments of the pump include multi-chamber bellows or other diaphragm based pumps which can rapidly deliver drug to the selected target tissue site.

14 Claims, 1 Drawing Sheet

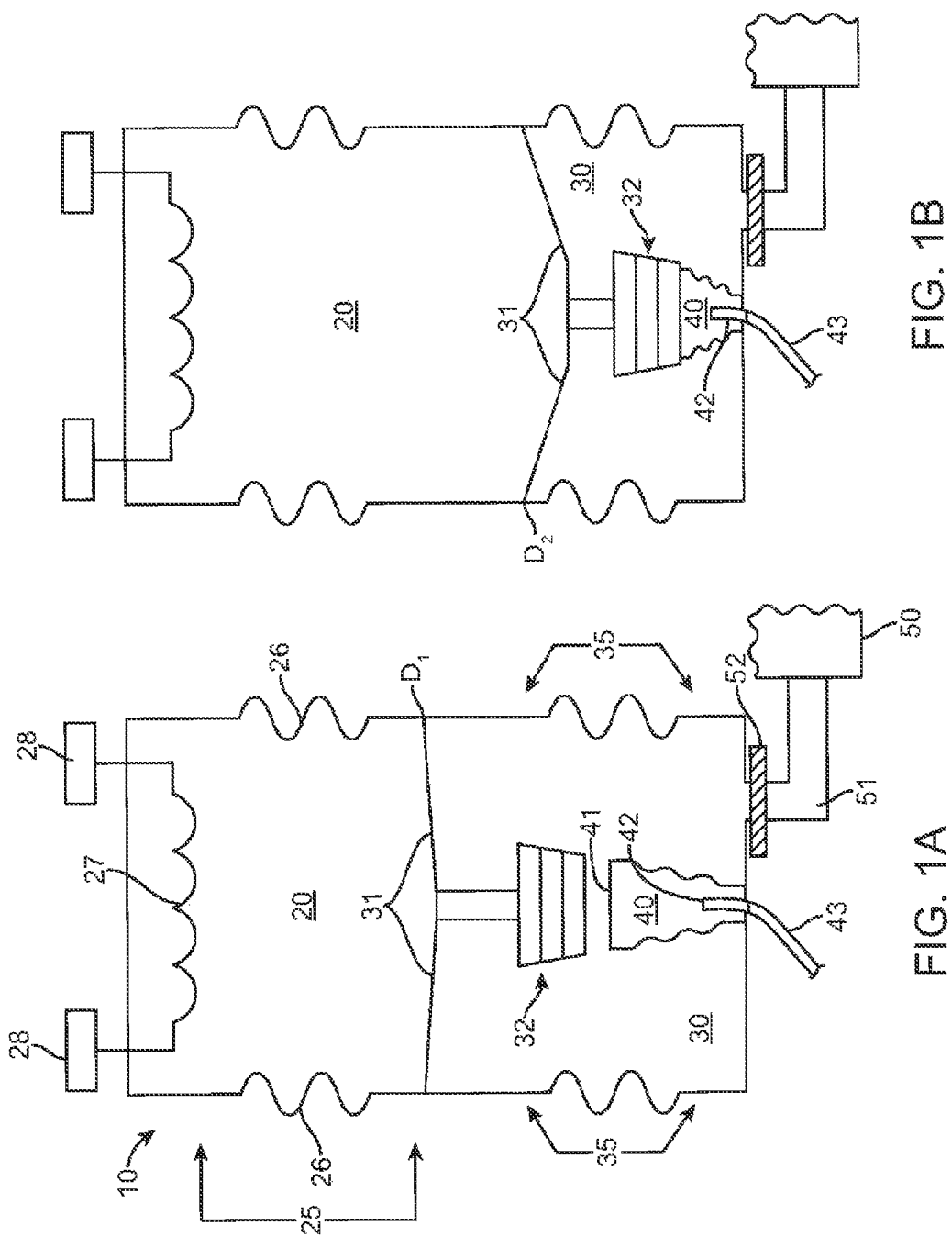

DIAPHRAGM DRUG PUMP

RELATED APPLICATIONS

This application claims benefit of priority to provisional U.S. Patent Application No. 61/099,196, filed Sep. 22, 2008; the aforementioned priority application being hereby incorporated by reference in its entirety.

TECHNICAL FIELD

Embodiments of the invention relate to drug pumps, and more specifically, to implantable diaphragm based drug pumps.

BACKGROUND

Many medical treatments use implantable drug pumps to deliver drugs to a specific target site of a patient, usually to avoid drug toxicity or injury to other tissue, organs or parts of the patient. However, in many cases, drug pumps are not practical because of size and power requirements for example, for intracranial drug delivery. Thus there is a need for improved implantable drug pumps.

BRIEF DESCRIPTION OF THE DRAWINGS

FIG. 1A shows a diaphragm based drug pump in a non-delivery state, according an embodiment.

FIG. 1B show a diaphragm based drug pump in a delivery state, according to an embodiment.

DETAILED DESCRIPTION OF THE INVENTION

Embodiments of the invention provides apparatus, systems and methods for using an implantable diaphragm based drug pump to deliver precisely controlled doses of drug to targeted sites in the body including without limitation the brain, digestive system, heart, blood stream, spinal column and other sites.

Embodiments of the invention provide apparatus, systems and methods for delivering various drugs using a diaphragm based drug pump which can deliver precisely controlled doses of drug to selected target tissue sites such as in the brain, spinal cord, digestive system, lung, heart or blood stream. Other target tissues sites are also contemplated, such as various subcutaneous and intramuscular sites throughout the body. Various embodiments include multi-chamber bellows or other diaphragm based pumps which can rapidly deliver drug to a target tissue site.

One embodiment of a diaphragm based pump for delivery drug to a target tissue site comprises a first chamber, a second chamber and a third chamber. Other numbers of chambers are also contemplated. The first chamber includes a diaphragm portion and a resistive heating element. The diaphragm portion is incorporated into two opposing walls of the chamber and typically comprises a bellows or other articulated structure allowing the chamber to contract and expand with changes in pressure. This is also the case for the second and third chambers. The resistive heating element can be coupled to a controller and power source for providing a power signal to the element. The first chamber is also filled with an inert gas such as helium. The second chamber is coupled to the first chamber and is separated by a wall. The second chamber also includes a bellows or other diaphragm portion as well as a piston valve which is coupled to the separating wall. The second chamber is also coupled to a drug reservoir by a channel such as a catheter or tubing. The reservoir contains a drug which can be in liquid or solid form and comprise a drug medium including the drug and various other compounds which can be in solid or liquid form. For liquid formulations, the drug will be dissolved in a drug solution. The solution can comprise the drug as well as various pharmaceutical excepients known in the art such as preservatives, emulsifiers, solubilisers and buffers to maintain a selected pH of the solution. Solid forms of the drug can include powder or pellets. The third chamber also includes a bellows or other diaphragm portion and a one way valve which can be mechanically linked to the piston valve by a shaft or other mechanical linkage. The one way valve can be connected to a catheter or other channel having a distal portion which is positioned in or adjacent the target tissue site or is coupled to a vein or artery so as to systemically deliver the drug.

FIG. 1A and FIG. 1B illustrate a diaphragm based pump for delivering drugs to a target tissue site in the body of a user. In FIG. 1A, the pump 10 is depicted as being in a non-delivery state, while in FIG. 1B, the pump 10 is depicted as being in a drug delivery state. In the non-delivery state, the pump 10 is capable of being triggered or signaled to deliver drugs into a patient. With further reference to FIG. 1A, an embodiment provides that the pump 10 includes a plurality of coupled expandable chambers, including a first chamber 20, a second chamber 30 provided adjacent to the first chamber, and a third chamber 40 provided within the second chamber 30. First chamber 20 includes a diaphragm portion 25, and a volume within the first chamber 20 that may be heated by a heating source 27. In one implementation, the heating source 27 corresponds to a resistive heating element. The heating source 27 may be controlled and heated by a power source 28, that triggers the first chamber 20 to be heated using a power signal. Other heating sources 27 may alternatively be used, such as an RF energy source, a microwave energy source, a peltier source, an optical energy source (e.g. infrared), a chemical energy source and other heating sources known in the art.

According to one or more embodiments, each chamber 20, 30 or 40 is expandable by extending a bellows, folded or extendable section of the respective chamber. In an embodiment, the diaphragm portion 25 of the first chamber 20 includes a bellows 26. In operation, first chamber 20 is selectively filled with an inert gas such as helium that is sufficiently expansive to expand or extend the bellows 26, so as to increase a length of the first chamber 20.

Second chamber 30 is positioned so that its top surface is adjacent and in contact to first chamber 20. The second chamber 30 is separated from the first chamber 20 at least in part by a wall 31. The second chamber 30 also includes a diaphragm portion 35, which is created by a bellowed or collapsible section of the sidewalls of the second chamber 30. The diaphragm portion 35 is formed into the sidewalls of the second chamber 30 between its top and bottom surfaces. At the bottom surface, the second chamber 30 is connected to a channel 51 that extends to a drug reservoir 50. A valve 52 is positioned to control flow into the channel 51, and further to preclude backflow.

In an embodiment, the second chamber 30 includes a piston valve 32 that extends inward from the top surface of the second chamber 30. The piston valve is configured to move inward (i.e. towards the bottom surface and the channel 51) to coincide with movement of the separation wall 31 with the first chamber 20. Depending on the implementation, more than one valve may be positioned to move inward with corresponding motion of the separation wall 31.

The third chamber 40 occupies a portion of the second chamber 30 extended from the bottom surface of the second chamber 30. The third chamber 40 is dimensioned to retain a certain volume of the drug when in the expanded state. As shown, the third chamber 40 is structured relative to the second chamber 30 so that its expansion coincides with the expansion of the second chamber 30 (so that both are expended when in the non-delivery state). The third chamber 40 is used to intake and expel the drug. Accordingly, the third chamber 40 includes an intake (e.g. an opening or openings) and an outlet from which drugs are expelled. To this end, the third chamber 40 includes an opening 41 that serves as a drug inlet, and an outlet valve 42 from which the drug is expelled. According to an embodiment, opening 41 is aligned with the piston valve 32, so that when the piston valve is descended, it effectively seals or closes the third chamber 40 by closing the opening 41. The outlet valve 42 of the third chamber 40 provides a conduit from which the drug is expelled. A catheter 43 or other conduit may extend from the outlet valve to carry the unidirectional flow of the drug to the target site of the patient.

FIG. 1B shows the pump 10 in the delivery state. In the delivery state, the first chamber 20 is extended as a result of the gas being heated by source 27. The first chamber 20 is extended from the first length D1 (non-delivery state) to the second length D2 (delivery state). According to an embodiment, a top and bottom boundary of the drug pump 10 may be structured to substantially hold the overall length dimension of the drug pump in both non-delivery and delivery states. As a result, the expansion of the first chamber 20 coincides with displacement of the separation wall 31 to contract the length of the second chamber 30 by a similar measure. A distance of separation between piston valve 32 and the opening 41 of the third chamber may be designed to be less than the amount that the second chamber 30 contracts as a result of the expansion of the first chamber. As a result, piston valve 32 presses third chamber 40 when the second chamber 30 is contracted, causing the third chamber to contract by a certain dimension. The piston valve 32 can collapse on the third chamber 40 when the second chamber 30 is contracted. As explained further, the reduction in the dimension of the third chamber 40 as a result of the contraction may be selected to correspond to a delivery volume of the desired drug, which is forced from the third chamber 40 into the valve 42 and out to the patient or target via catheter 43.

With reference to both FIG. 1A and FIG. 1B, when pump 10 is in operation, the non-delivery state provides that the first chamber 20 is in a non-expanded state, the second chamber 30 is in an expanded state, and the third chamber 40 is in an expanded state. When in operation and in the non-delivery state, the second chamber 30 is at least partially filled with drug liquid from the reservoir 50. In one embodiment, the fluid of the second chamber 30 is drawn by vacuum or suction force as a result of the pump 10 transitioning from the delivery state to the non-delivery state (meaning the second chamber 30 expands to the non-expanded state). In one implementation, when the pump 10 is initially connected for use, it is in the delivery state and natural expansion is used to contract first chamber 20 and expand the second chamber 30. As an alternative or addition, and as described below, the material that forms the chambers may be designed to bias and return to the non-delivery state after being forced into the delivery state (for delivery of the drug). In either case, the transition of the chambers from the non-delivery state to the delivery state effectively draws out the drug in liquid form from the reservoir 50, so as to partially fill the second chamber 30 (and potentially the third chamber 40). As still another alternative or addition, the reservoir 50 may be dimensioned and positioned to provide pressure against a valve 52 to facilitate flow of the drug from the reservoir 50 to the second chamber 30 when the second chamber is extended (or transitioned into the extended state).

Transition from the non-delivery state to the delivery state occurs when the first chamber 20 is expanded. As mentioned, when expansion of the first chamber 20 occurs, the separation wall 31 of the first chamber moves outward to force the second chamber 30 to contract. With movement of the wall 31, the piston valve 32 is moved to press against the opening 41 of the third chamber (so as to seal the third chamber shut). At same time, contraction of the second chamber 30 may press or move more drug liquid (or solid) into the third chamber 40 via the opening 41. As the first chamber 20 expands to its maximum operational volume, the piston 32 presses the third chamber 40 to contract downward. The reduction in the dimension of the third chamber 40 causes a volume of the drug liquid to be forced out of the third chamber 40 through the valve 42 and to the patient or target via the catheter 43 (or other conduit). In an embodiment, the third chamber 40 may be sized or configured to contract by an amount that corresponds substantially to a volume or cyclic dosage of the drug that is to be delivered. In use, some embodiments allow third chamber 40 to function as a metering chamber or element 40 to meter out a controlled dose of drug for delivery to the selected target tissue site(s).

According to an embodiment, in a short period of time following delivery of the drug liquid, the gas of the first chamber 20 cools, so that the bellows 25 of the first chamber springs back to an unbiased or natural state. This in turn causes the separation wall 31 to pull upward, returning the second chamber 30 into its normal or default expanded state. This in turn pulls back piston valve 32 from the opening 41 of the third chamber 40. The piston valve 32 can be released from and elevated away from the third chamber 40 when the second chamber 30 is expanded. At about the same time, the expansion of second chamber 30 (and/or third chamber 40) creates a vacuum pressure which acts to pull the drug liquid from reservoir 50 and into the second and/or third chamber for use in the next pumping cycle.

Using a controlled heating source, heating element 27 may be configured to be actuated cyclically or repeatedly over a given duration (including short durations). In one embodiment, cyclic actuation enables a continuous or near continuous dose of drug to be delivered over a select time period. A duty cycle approach can also be used to allow for the controlled delivery of the drug over a selected time period while still allowing sufficient time for each chamber to recoil or otherwise return to its natural resting state.

According to one or more embodiments, the pump 10 may be engaged to deliver drug liquid in extremely fast periods, for example, tenths to hundredths of a second or less. This rapid response allows for the delivery of drug soon after an input signal indicating the occurrence or imminent occurrence of a biological event such as the onset of an epileptic seizure, migraine headache or heart attack. In the case of an epileptic seizure, for example, the rapid delivery of a drug such as an anti-seizure drug can be configured to actually prevent or attenuate the epileptic seizure. Suitable anti-seizure drugs can include without limitation phenytoin sodium and Furosemide. In other embodiments, pump 10 can be adapted for the delivery of insulin (either in liquid or solid form) into the blood stream, intramuscularly, or into the lungs. In such embodiments, pump 10 can be coupled to a glucose monitoring and control system which can either be external or implanted. For external glucose monitoring systems, the pump can be configured to receive an RF or other wireless signal from the glucose monitoring and control system. In other embodiments, pump 10 can be configured for the delivery of various pain medications and can be configured to be patient activated with controls to limit the number of self administered doses.

Variations and Alternatives

In one or more embodiments, pump 10 can also be configured to be used in conjunction with conventional IV drug delivery pumps, for example so that pump 10 initiates the rapid delivery of a drug (e.g. an anti seizure medication such as phenytoin sodium or Furosemide) which is later supplemented by delivery from the conventional IV delivery pump. In such embodiments, pump 10 and the IV delivery pump can be controlled by a common controller such as a microprocessor. In still other embodiments, multiple pumps 10 can be distributed in various location throughout the body (e.g., GI system, the vascular system, the brain and intramuscularly) so as to deliver one or more drugs in multiple locations. In these embodiments, pumps 10 can be electronically controlled by a common controller which initiates delivery from a selectable number of pumps 10. The controller can include one or more in vivo sensors for monitoring a bio-analyte to be controlled such as blood glucose. The controller can also be programmed to use delivery of drug from multiple pumps 10 either concurrently or in a selectable sequence. Use of such a multiple pump delivery system allows for a more rapid, precise and homogenous delivery of drug to one or more target tissue sites or throughout the body (e.g., for insulin). It also allows for the concurrent delivery of multiple drugs to rapidly treat the onset of a sudden medical condition such as epileptic seizure, arrhythmias, acute angina, heart attack or like conditions. For example, in the case of arrhythmias, pump 10 could be used to rapidly dispense calcium channel blockers (e.g., verapamil) or beta blockers (e.g., propranolol hydrochloride) or a combination thereof, directly into the heart and/or the blood stream. For acute angina or a heart attack, pump 10 could be used to rapidly dispense a dose of a vasodialator such as nitroglycerine, a betablocker such as propranolol or a calcium channel blocker such as verapamil or a combination thereof directly into the heart and/or into the blood stream.

While numerous embodiments described herein provide for use of a heating element in order to expand the first chamber 20, other embodiments may utilize other mechanisms to create sufficient expansion of that chamber (and resulting contraction of the second chamber 30). In one embodiment, for example, first chamber 20 is coupled to a source of gas that can be used to inflate the first chamber 20. As an alternative or variation, an electrically operated micropump may be connected to the first chamber 20 to cause either expansion or contraction.

In an embodiment, a cooling mechanism may be provided for use in connection with the heating element in order to enable the first chamber 20 to cool, and thus contract when heated into expansion. The cooling mechanism may be provided passively, such as through ventilation, or actively through an element that can actively cool (. For passive cooling, the cooling mechanism can include various conductive elements such as cooling fins. For active cooling, the cooling mechanism can include gaseous injection, a joule thompson device, a peltier effect device.

As an alternative to use of a heating element to expand the first chamber 20, other embodiments may utilize other forms of expanders, such as those that use pumps or gaseous injections.

Pump 10 can be used to deliver any number of drugs or combinations of drugs. In various embodiments, the drugs which can be delivered by pump 10 can include without limitation: various amino-sulfonyl-benzoates compounds and analogs (eg. furosemide, bumetanide, torsemide, and ethacrynic Acid), phenytoin sodium (e.g., DILATIN), antibiotics (e.g., penicillin, ampicillin, erythromycin, ciprofloxacin, vancomycin, etc), beta blockers, calcium channel blockers, potassium/sodium channel blockers, vasodialators, antibodies, proteins, polypeptides, insulin and other glucose regulating compounds, various anti-diarrheal drugs (e.g., Loperamide oxide) various chemotherapeutic agents (e.g., doxorubicin), various hormones having birth control properties (e.g., estrogen and progesterone as well as combinations thereof). The delivered drug can also include various pro-drugs which are metabolized into their active form once released into the body. Suitable pro-drugs can include anti-viral nucleoside analogs, lipid-lowering statins, antibody-directed/gene-directed enzyme prodrugs for chemotherapy, etoposide phosphate, valganciclovir and fosamprenavir.

Conclusion

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the drug pump described herein can be sized and otherwise adapted for placement in variety of locations in the body including without limitation the skull, spinal column, abdominal cavity, the chest cavity, the heart, extremities and any number of subdermal or intramuscular locations. They can also be sized and otherwise configured for various pediatric and neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A drug pump comprising:
   multiple expandable and contractable chambers, including at least a first chamber, a second chamber and a third chamber, wherein the first chamber and the second chamber are positioned so that expansion of the first chamber causes contraction of the second chamber, and contraction of the first chamber causes expansion of the second chamber;
   wherein the second chamber is structured to connect to a reservoir for retaining a drug medium;
   wherein the third chamber is formed with the second chamber and includes (i) an intake for the drug medium, and (ii) an outlet to expel the drug medium; and
   a member provided with the second chamber to extend inward and collapse on the third chamber when the second chamber is contracted with expansion of the first chamber, so as to cause the third chamber to contract and expel the drug medium.

2. The drug pump of claim 1, wherein the member is provided with the second chamber to release from and elevate away from the third chamber when the second chamber is expanded.

3. The drug pump of claim 2, wherein the second chamber is connectable to the reservoir to create a suction pressure when the second chamber is moved from being contracted to being expanded, so as to draw the drug medium into the second chamber and enable the drug medium to enter the third chamber via the intake of the third chamber.

4. The drug pump of claim 3, wherein the intake for the drug medium of the third chamber corresponds to an opening that is sealed by the member when the second chamber is contracted.

5. The drug pump of claim 1, further comprising an expansion mechanism that is coupled to the first chamber in order to cause the first chamber to expand and to cause the second chamber and third chamber to contract.

6. The drug pump of claim 5, wherein the expansion mechanism corresponds to a heating element.

7. The drug pump of claim 6, further comprising a control element to control when the first chamber is heated into expansion.

8. The drug pump of claim 7, wherein the control element controls the heating element in heating the first chamber into expansion in accordance with a duty cycle.

9. The drug pump of claim 1, wherein at least one of the first chamber, second chamber, and third chamber includes sidewalls that are formed at least in part by a bellows structure to enable the respective first, second or third chamber to expand and contract.

10. The drug pump of claim 1, wherein each of the first, second and third chambers include sidewalls that are formed at least in part by a bellows structure to enable the respective chamber to expand and contract.

11. A drug pump comprising:
multiple expandable and contractable chambers, including at least a first chamber, a second chamber and a third chamber, wherein the first chamber and the second chamber are positioned so that expansion of the first chamber causes contraction of the second chamber, and contraction of the first chamber causes expansion of the second chamber;
wherein the second chamber is structured to connect to a reservoir for retaining a drug medium;
wherein the third chamber is formed with the second chamber and includes (i) an intake for the drug medium, and (ii) an outlet to expel the drug medium; and
a member provided with the second chamber to extend inward and collapse on the third chamber when the second chamber is contracted with expansion of the first chamber, so as to cause the third chamber to contract and expel the drug medium, and
a conduit that extends from the second chamber to the reservoir.

12. The drug pump of claim 11, further comprising a valve provided on the conduit to prevent backflow into the reservoir.

13. The drug pump of claim 11, further comprising a control element to control when the first chamber is expanded.

14. The drug pump of claim 11, wherein the member provided with the second chamber is configured to extend inward and contact the third chamber by collapsing on the third chamber.

* * * * *